US006741976B1

(12) United States Patent
Tuzhilin (10) Patent No.: US 6,741,976 B1
(45) Date of Patent: May 25, 2004

(54) METHOD AND SYSTEM FOR THE CREATION, APPLICATION AND PROCESSING OF LOGICAL RULES IN CONNECTION WITH BIOLOGICAL, MEDICAL OR BIOCHEMICAL DATA

(76) Inventor: Alexander Tuzhilin, 110 Bleecker St. #17B, New York, NY (US) 10012

( * ) Notice: Subject to any disclaimer, the term of this patent is extended or adjusted under 35 U.S.C. 154(b) by 328 days.

(21) Appl. No.: 09/604,213

(22) Filed: Jun. 27, 2000

Related U.S. Application Data (60) Provisional application No. 60/141,816, filed on Jul. 1, 1999.

(51) Int. Cl.$^7$ ............................ G06F 17/00; G06F 15/18
(52) U.S. Cl. ............................ 706/48; 706/47; 706/61; 706/924
(58) Field of Search ................... 706/61, 59, 47, 706/50, 45, 12, 16, 20, 48, 924; 707/104.1, 3, 102; 702/19

(56) References Cited

U.S. PATENT DOCUMENTS

| | | | | | |
|---|---|---|---|---|---|
| 5,446,885 | A | * | 8/1995 | Moore et al. | 707/103 R |
| 5,630,127 | A | * | 5/1997 | Moore et al. | 707/103 R |
| 5,875,285 | A | * | 2/1999 | Chang | 706/53 |
| 6,006,223 | A | * | 12/1999 | Agrawal et al. | 707/5 |
| 6,108,635 | A | * | 8/2000 | Herren et al. | 705/2 |
| 6,139,494 | A | * | 10/2000 | Cairnes | 600/300 |
| 6,230,142 | B1 | * | 5/2001 | Benigno et al. | 705/3 |
| 6,236,978 | B1 | * | 5/2001 | Tuzhilin | 705/26 |
| 6,292,797 | B1 | * | 9/2001 | Tuzhilin et al. | 707/6 |
| 6,304,869 | B1 | * | 10/2001 | Moore et al. | 707/3 |
| 6,308,172 | B1 | * | 10/2001 | Agrawal et al. | 707/5 |
| 6,311,173 | B1 | * | 10/2001 | Levin et al. | 706/21 |
| 6,327,581 | B1 | * | 12/2001 | Platt | 706/12 |
| 6,453,241 | B1 | * | 9/2002 | Bassett et al. | 702/19 |
| 2001/0023419 | A1 | * | 9/2001 | LaPointe et al. | 706/15 |

OTHER PUBLICATIONS

Saraee et al., "easyMiner: Data Mining in Medical Databases", IEE Colloquium on Intelligent Methods in Healthcare and Medical Applications, Oct. 1998, pp. 7/1–7/3.*
Silberschatz et al., "User–Assisted Knowledge Discovery: How Much Should the User Be Involved", Proceedings of the SIGMO Workshop n Research Issues on Data Mining and Knowledge Management, Jun. 1996.*
Padmanabhan et al., "Pattern Discovery in Tempral Databases: A Temporal Logic Approach", 2nd International Conference on Knowledge Discovery and Data Mining, 1996.*
Silberschatz et al., "What Makes Patterns Interesting in Knowledge Discovery Systems", IEEE Transactions on Knowledge and Data Engineering, Vol 8, Iss 6, Dec. 1996.*

(List continued on next page.)

*Primary Examiner*—John Follansbee
*Assistant Examiner*—Kelvin Booker
(74) *Attorney, Agent, or Firm*—Mitchell A. Stein, Esq.; Stein Law, P.C.

(57) ABSTRACT

A method and system for the analysis of biological, medical and/or biochemical data having values for each of a plurality of attributes, having a receiving portion for receiving the data and entering it into a storage arrangement like a relational database in accordance with the values and attributes of the data; a calculating portion for determining discrete bins for at least one of the attributes for the data in accordance with the values of the data entered in the storage arrangement; a re-organizing portion for re-organizing the data in the storage arrangement in accordance with the discrete bins; a data mining portion for mining the organized data in the storage arrangement to determine sets of applicable logical rules; and a processing and presenting portion for logical rules or groups of logical rules. The processing portion further involves the application of at least one operator to create a subset of rules in an iterative manner. The operators are filtering operators, clustering operators, data mapping operators, and/or data characterization operators.

23 Claims, 3 Drawing Sheets

OTHER PUBLICATIONS

Tuzhilin et al., "Querying and Controlling the Future Behavior of Complex Objects", 5th International Conference on Data Engineering, Feb. 1989, pp. 434–442.*

Vaughn et al., "Interpretation and Knowledge Discovery From A MLP Network That Performs Low Back Pain Classification", IE Colloquium on Knowledge Discovery and Data Mining, May 1998, pp. 2/1–2/4.*

Mani et al., "Generating Models of Mental Retardation from Data with Machine Learning", Proceedings of Knowledge and Data Engineering Exchange Workshop, Nov. 1997, pp. 114–119.*

Padmanabhan et al., "Unexpectednes as a Measure of Interestingnes in Knowledge Discovery", NEC Research Index, Decisio Support Systems, 1999.*

Silberschatz et al., "On Subjective Measures of Interestingness in Knowledge Discovery", Knowledge Discovery and Data Mining, 1995, pp. 275–281.*

Padmanabhan et al., "A Belief–Driven Method for Discovering Unexpected Patterns", Knowledge Discovery and Data Mining, 1998, pp. 94–100.*

Tsumoto, S., "Knowledge Discovery in Medical Databases Based on Rough Sets and Attribute–Oriented Generalization", IEEE World Congress on Computational Intelligence, May 1998, Vol 2, pp. 1296–1301.*

Mueller, A., "Fast Sequential and Parallel Algorithms for Association Reul Mining: A Comparison", NEC Research Index, 1995.*

Tsur et al., "Query Flocks: A Generalization of Association–Rule Mining", Proceedings of the 1998 ACM SIGMOD International Conference on Management of Data, 1998, pp. 1–12.*

* cited by examiner

METHOD AND SYSTEM FOR THE CREATION, APPLICATION AND PROCESSING OF LOGICAL RULES IN CONNECTION WITH BIOLOGICAL, MEDICAL OR BIOCHEMICAL DATA

CONTINUING AND PRIORITY DATA

This application claims priority form its Provisional Application, Serial No. 60/141,816, filed on Jul. 1, 1999.

FIELD OF THE INVENTION

The present invention relates to the field of sorting and analysis of vast amounts of scientific data, and more particularly to methods and systems for the discretizing of biological, medical or biochemical data and generation of logical rules from that data, followed by processing of the generated rules.

BACKGROUND OF THE INVENTION

Scientists create vast amounts of raw data. The sheer volume of such data renders difficult, if not impossible, the ability to draw complete conclusions from that data. Accordingly, mathematicians are requested to develop processes to analyze such data and, in particular, to study, organize, and determine rules (also called logical statements) for the presentation and analysis of such raw data in ways that can become scientifically important by exposing rules (and their bases) in a manner that permits conclusions to be drawn.

Traditional approaches to the creation of scientific data (and, more importantly, biological, medical and biochemical data) followed by human analysis fall short because literally thousands if not millions of data points are created. The intuitive ability of the human mind to analyze such data and draw logical, rational and appropriate conclusions has been emulated by computer-assisted analytical techniques including, e.g., the creation and analysis of logical rules for such data.

With respect to biological data in particular, vast amounts are created virtually daily. Within the class of biological data, lies a subclass of genetic data. With respect to genetic data, which is a particular segment of the biological community, the Human Genome Project and its progeny have created a simply unmanageable quantity of potentially relevant information relating to gene sequencing and expression. One of the major goals of molecular biology is to study such data and determine how different genes regulate one another. Thus, a major research effort has been targeted towards understanding and discovering gene regulation patterns. Likewise, huge amounts of medical data is created by laboratory and other analyses of medically significant biochemical moieties and their variations. The coding of protein interactions (and their DNA/RNA interfaces for synthesis) in the field of proteomics also results in significant data creation. Not all the data is relevant, yet some of the data that might appear at first human blush to be marginal, when combined with other data points, can reveal logical rules with appropriate statistical reliability, thereby enhancing the ability to modulate the experimental protocols employed or the conclusions determined.

One of the main techniques used by biologists for the creation of data concerning genetic expression is the oligonucleotide microarray method, which has reached popularity in the last few years. This technique permits biologists to produce large quantities of gene microarray data points that profile gene expressions under different conditions, at different times during development or in the presence of different factors that include, without limitation, drugs, environmental conditions, biochemical compounds, and the like. Typically, biologists generate a set of tests applying this method to a biological sample, where a single test would contain information on the expression levels of genes in the sample, and the number of tests would result in a range of measurements from a few dozen to a few hundred.

Gene regulation may be understood by measuring the amounts of different gene products produced by a cell. This production process, called gene expression, creates as a product a form of RNA. The oligonucleotide microarray method is a standard method employed to measure amounts of this form of RNA, in which this form of RNA is hybridized to an oligonucleotide microarray that allows the measurement of expression levels of up to tens of thousands of genes in a single experiment. From the computational point of view, the expression level is represented as an arbitrary real number. Therefore, the result of a single experiment is an array of "N" real numbers, where "N" remains the same across different experiments and depends upon the genes sought to be measured by the experimenter.

In order to discover how different genes regulate one another, biologists typically conduct multiple experiments to determine the manner in which different gene expressions change depending upon the type of tissue, age of the organism, therapeutic agents, and environmental conditions. Moreover, biologists are more interested in the method by which gene expressions vary in these experiments relative to normal expression levels in an organism, rather than absolute values of gene expression.

Accordingly, the manner in which patterns of genetic output change across different samples reflect underlying biological processes in the organism whose genes are being studied. It is of crucial importance for biologists to understand these biological processes, and a major research effort has been launched towards the discovery and biological interpretation of gene regulation patterns. As a result, millions of data points have been generated.

Typical data analysis techniques for handling vast amounts of oligonucleotide microarray data are based mainly on manual selection, querying and clustering techniques. Manual selection of patterns is usually performed by a direct "eyeballing" of the data by a person with some amount of experience or specialized expertise. This traditional approach is virtually impossible when the size of the database gets too large.

Database-querying techniques include SQL querying methods, and permit the data analyst to apply pertinent queries to the data and receive responsive information. While such techniques are effective in instances when the analyst is cognizant of the attributes of the data and thus can determine the queries, when the data is vast in size and the queries are less obvious, these techniques prove to be ineffective.

Clustering methods are shown in, for example, Eisen, et al. "Cluster Analysis and Display of Genome-wide Expression Patterns," *Proc. Nat'l. Acad. Sci. USA*, 95(25):14863–8, 1998, and also include self-organizing maps as shown in Tamayo, et al., "Interpreting Patterns of Gene Expression with Self-Organizing Maps: Methods and Application to Hematopoetic Differentiation," Proc. *Nat'l. Acad. Sci. USA*, Vol 96, pp. 2907–2912, March 1999. Such methods group genes into clusters that exhibit "similar" types of behavior in the experiments. These clustering methods allow biologists to design experiments helping them to understand further the relationships among the underlying data points, and hence the genetic expressions shown by those data points. However, such traditional clustering methods fail to provide deep insights into specific relationships among genes and biological processes in the cell because the clusters are, by definition, broad categories.

Support vector machines ("SVM's") have been employed to overcome the problems associated with the querying, clustering and self-organizing map approaches, as shown in Brown, et al., "Knowledge-Based Analysis of Microarray Gene Expression Data by Using Support Vector Machines," in *PNAS*, vol. 97, Issue I, pages 262–267, Jan. 4, 2000. In particular, the SVM method described in Brown, et al. builds a gene classifier based on some training data by using SVM methods that draw hyperplanes that separate different classes of data (e.g., positives from negatives). Then these classifiers are used to identify unknown functions of genes. SVM methods seek to solve an important but very specific problem of identifying functions of genes based upon predetermined classifications of functions using supervised machine learning methods. There is, however, much more to the analysis of biological and genomic data than just the identification of gene functions.

It is thus an object of the present invention to overcome the shortcomings of the prior art and provide a mathematical system and method that employs a computer for processing large amounts of biological, medial and/or biochemical data through the process of discretizing this data, generating logical rules from such discretized data, and processing of those rules by the system in a manner that presents rules of greatest relevance.

SUMMARY OF THE INVENTION

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

The present invention relates to a method and system for the analysis of biological, medical and/or biochemical "raw" data, and more particularly to the creation of discrete values for each of such data points based upon a plurality of attributes, followed by creation of rules and subsequent processing of these rules. The steps involved in the instant invention include receiving the raw data and entering such data into a storage arrangement including, e.g., a relational database, in accordance with the values and attributes of the data; determining discrete bins for at least one of the attributes for the data in accordance with the values of the data entered in the relational database for each of the attributes; discretizing the data in the database by replacing each of the data points in the database with a number reflecting the appropriate bin in which each such point is found; mining the discretized data in the relational database to determine sets of applicable logical rules including, e.g., association rules; processing the logical rules at least once; and presenting the processed logical rules, with or without the discretized and raw data. The number of bins is a small number "n," in which $1<n \leq 100$, preferably $n \leq 10$, and more preferably $n = 3$.

The discretization process converts numeric values, e.g., gene expression data from a particular experiment, into a discrete value corresponding to a specific bin. The number of such bins and the boundaries between them can be determined using methods known to someone of ordinary skill in the art, or determined mathematically by establishing the full range of data values and parsing boundaries between them using known methods. Once the appropriate bin is determined, the instant method and system will place a tag upon each data point indicative of the bin in which that data point is to be placed.

As a result of the discretization step, boundaries between data points are determined and each of the raw values of data are then converted into discrete values. For the particular preferred embodiment of expression levels of individual genes in a single experiment, these values are preferably represented with three different states: unchanged (denoted as #), upregulated (denoted as ↑), and downregulated (denoted as ↓). Therefore, each experiment is re-represented with a vector of N genes taking one of these three values (#, ↑, ↓). Each entry in a relational database has, for each attribute, preferably one of these three values. Assuming that there are M experiments (or attributes) and N genes, the relational database can be represented by an M×N matrix of n values. After creating this M×N matrix, the inventive process next generates logical rules for gene expression.

Although the invention preferably possesses three discrete bins for discretization of the genetic attributes (upregulated, downregulated, and unchanged), it is not limited to this specific case. In fact, the system and method can accommodate any other number of gene expression states or scientific attributes. For example, genes can have binary states (yes/no), or arbitrary n-valued states (e.g. n=4, 5, etc.).

Once the data is discretized, the inventive system and method then "mines" the data to determine logical rules for that data, including degrees of reliability of the logical rules based upon the underlying data. Data mining techniques are known in the art, including those stated in Agrawal, et al., "Fast Discovery of Association Rules," in Fayyad, U. M., et al., *Advances in Knowledge Discovery and Data Mining* (AAAI Press, 1996, Chapter 12) (hereinafter "Agrawal, et al.") which are especially usefull to the instant invention.

The data mining step creates a plethora of logical rules especially for genomic data where N is very large. Where the underlying biological, medical or biochemical data is voluminous, the expectation is the creation of a smaller, but still quite large, subset of logical rules. Hence, it is important to sift through this large mass of logical rules to enable the presentation of those that are truly of interest. Accordingly, the instant invention provides for iterative processing of the created rules by way of a plurality of different operators, described in greater detail below.

The inventive operators include filtering operators (MATCH(S,T), MISMATCH(S,T), and CONTRADICT(S, T)) in which S is a set of logical rules, and T is a template. Also presented are clustering operators. Also included, are a set of data mapping operators (TRANS_MATCH(D,T,C) and TRANS_MISMATCH(D,T,C), in which D is a data set, T is a template, and C is a matching condition "for all" or "for any." Lastly, included is a data characterization operator (DATA-CHAR(D,S,R)), wherein D is a set of transactions, S is a structure, and R is a set of rules.

It should be appreciated that the system and method described are not limited to the gene expression problem. In fact, the invention is applicable to biological, medical or biochemical data for which the discovery of large numbers of logical rules are a necessary consequence of the analysis of volumes of underlying data. As a result of the invention and its employment of the operators to the logical rules produced from the discretized data, a smaller population of rules is produced that are of greater importance and reliability, and the basis for creating this population can be iteratively adapted if other indicia of significance are considered. The invention is particularly useful in applications having relatively few data points/records (e.g., measured in hundreds) and a huge number of attributes/fields/variables (e.g., measured in 10's or even 100's of thousands of attributes). Obviously, the gene expression problem constitutes one such application. Other applications include analysis of biochemical compounds, proteomics (protein interaction) and efficacy of drugs and their analogs.

Other features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

The present invention is further described in detail below with reference to the accompanying drawing, in which.

DESCRIPTION OF THE PREFERRED EMBODIMENTS

Figure 1:
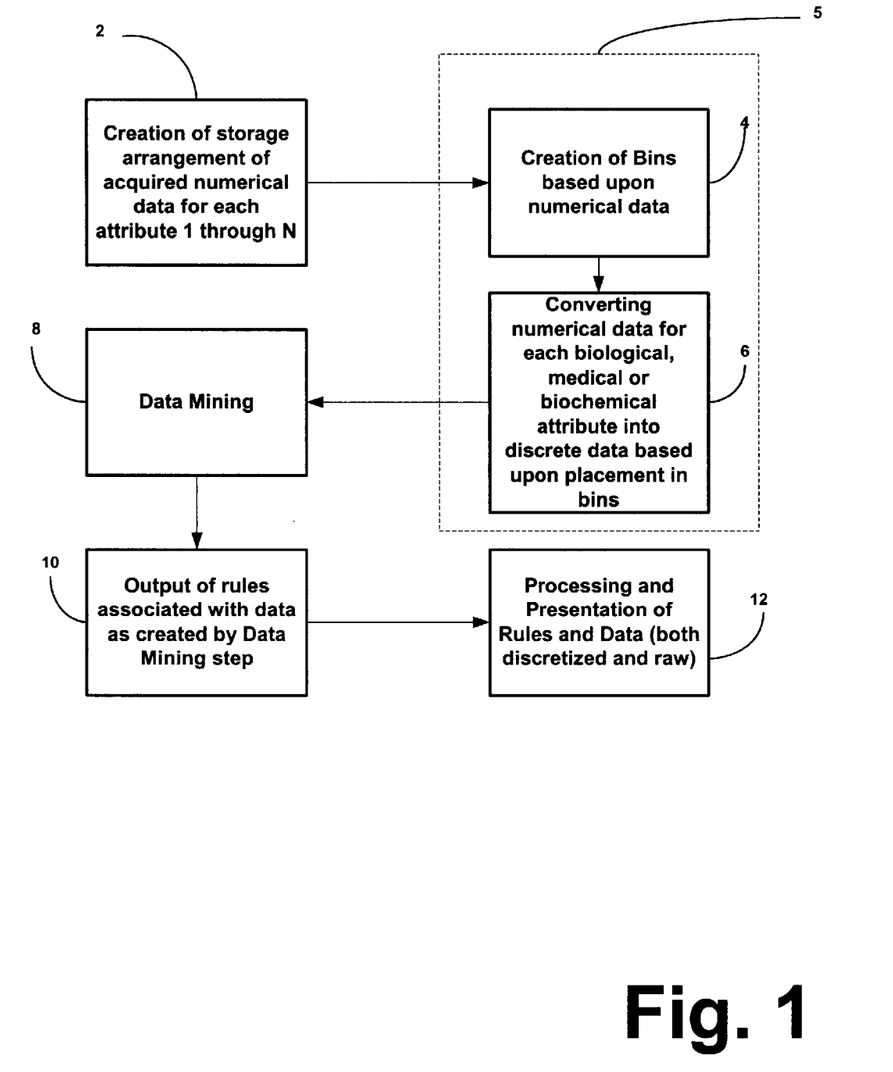
FIG. 1 is a flow diagram of the main steps and stages of the method and process of the preferred embodiment of the subject invention.

In FIG. 1, step 2, the numerical data received from a biological, medical or biochemical experiment, having fields (attributes) 1 to N, is stored in a large storage arrangement, including, e.g., a relational database. Thereafter, preprocessing of this data occurs via step 5.

Preprocessing, in a preferred embodiment, includes, at step 4, the creation of bins based upon the numerical data. In particular, and by way of example, the scope of data points corresponding to a particular predetermined field are ordered linearly, and bisected in accordance with their means and standard deviation to create a number of bins. Typically, in the preferred embodiment concerning gene expression data, there are three such discrete bins: unchanged, upwardly modified (regulated), and downwardly modified (regulated). The data is migrated, tagged or converted into each one of these three discreet bins, for the preferred embodiment, and n bins, for the invention in general, at step 6. Ordinarily, however, the raw data is not replaced, for then it would be lost and no longer accessible for further viewing and/or analysis.

Step 8 comprises typical methods of data mining that generates logical rules from the data discretized at step 6, by employing methods known to those of ordinary skill in the art. These rules are output in step 10. At step 12, processing of the rules occurs, as further described below and as shown in FIG. 2, in order for processed rules and data (both discrete and raw) to be presented.

One method of performing data mining in accordance with the invention at step 8 is to generate all the association rules satisfying minimal levels of confidence and support. In order to achieve this result, one can employ the algorithms shown by, for example, Agrawal, et al. However, it should be recognized that such algorithms are less than perfect when applied to a large database, because they will result in the creation of a huge body of rules, after running for a prolonged period of time. As a result, a very large number of rules are discovered at step 10, often measured in the millions. Accordingly, post-processing of rules per step 12 is required in order for there to be meaningful analysis of discovered rules and selection of those that are of interest.

Figure 2:
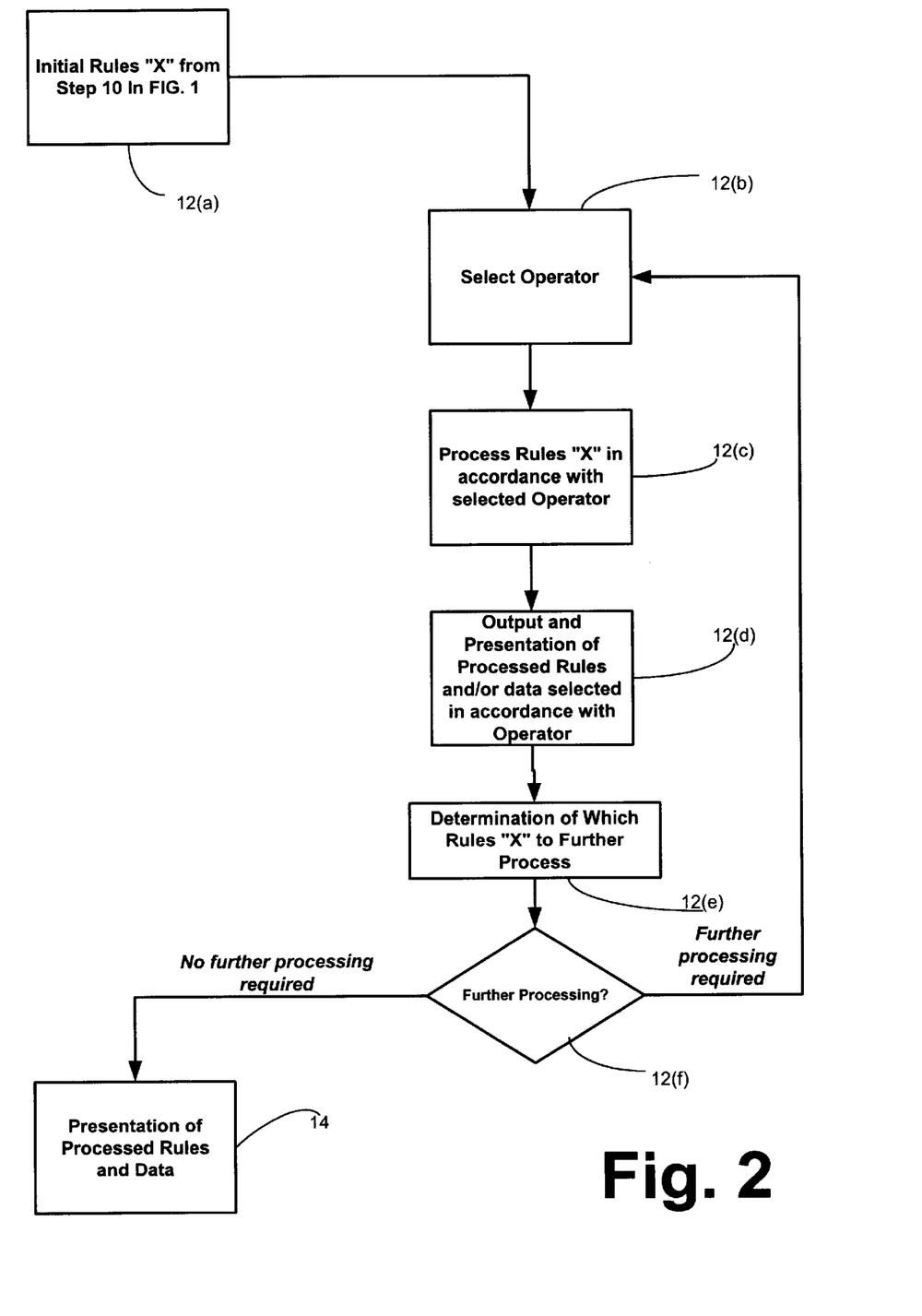
FIG. 2 is a flow diagram of the sub-steps and sub-stages of the multiple processing steps and stages shown in FIG. 1.

Digressing from FIG. 1, step 12, to FIG. 2, there are shown the particular steps involved in processing of the logical rules via step 12. In particular, initial rules "X" associated with data are received via step 12(a) from step 10 in FIG. 1. Rule processing operators are first selected by step 12(b). Rules are processed in accordance with the selected operator(s) at step 12(c). Then, the rules and/or data selected in accordance with the operator(s) are output at step 12(d) for examination. Determinations are then made at step 12(e) of which rules "X" to further process. If no further processing is desired, as determined at step 12(f), then the system presented the processed rules and data at step 14. Otherwise, further processing is performed, and an operator is selected again at step 12(b). In this manner, step 12(e) provides for the determination of which set of rules "X" to further process, and step 12(f) provides the determination of when to cease further processing.

The Operators

The rule processing operators described in steps 12(b) through 12(f) take different forms and include, without limitation, filtering, data mapping, rule clustering and data characterization operators.

Filtering Operators

Filtering operators are selected for the particular scientific problem including, e.g., the gene regulation problem. Since some of these operators are based on the concept of a pattern template, in order to define pattern templates, taxonomies for attributes are employed. For example, the user can impose a taxonomy on the list of genes by grouping them into the classes of Metabolic, Structural, and Regulatory genes. Then a pattern template is a rule $$A_1 \wedge A_2 \wedge \ldots A_k \rightarrow A_{k+1} \tag{1}$$

where each $A_i$ is either an attribute, name, a class name or an expression C+ or C* corresponding, respectively, to one or more and zero or more instances of the class C. Such a template defines a class of rules that satisfy the constraints imposed by this template. For example, consider a pattern template Gene__, Metabolic__Gene+→Structural__Gene specifying associations between Gene__1, one or more genes from the group of metabolic genes (irrespective of any particular gene), and a gene from the group of structural genes. In this template, Gene__is an attribute, and Metabolic__Gene and Structural__Gene are classes in the gene taxonomy. Then if Gene__X is a member of the class of metabolic genes and Gene__Y is a member of the class of structural genes, then the logical rule Gene__, Gene__X→Gene__Y matches the specified pattern template. Pattern templates are known to one of ordinary skill in the art, having been studied in Klemettinen, et al. "Finding Interesting Rules from Large Sets of Discovered Association Rules," appearing in the Third International Conferences on Information and Knowledge Management, pages 401–407, Nov. 29–Dec. 2, 1994. Other methods of implementing pattern templates will be known to those of ordinary skill in the art by studying the instant invention, and can be employed without deviating from the scope of the invention as described herein and covered by the claims appended hereto.

The filtering operators take a set of rules and select a subset of these rules based on the specified filtering criteria. Different types of filtering criteria give rise to specific filtering operators. These filtering criteria include but are not limited to operators Match, Mismatch, and Contradict. These filtering operators are defined as follows:

1. MATCH(S, T). This operator selects all the logical rules in set S that match pattern template T, and returns these rules. One inventive implementation of template T consists of a disjunction of the conjunctive clauses of the form <rule-part> <op> {<clause>}, where <rule-part> is either BODY or HEAD, <op> is one of the standard set-theoretic operators known to someone with an ordinary skill in the art. These operators include, but are not limited to, the operators ($\leq, \geq, >, <$, etc.) or their natural language equivalents. Also, <clause> can have the structure as in the body of rule (1), where each clause is of the form <exp> <eq> <value>, where <exp> can either be an attribute or a class, <eq> is either=, $\neq$, $=_\exists$, or $=_\forall$ and <value> takes one of the values $\uparrow$, $\downarrow$, #, or * (* is a wildcat symbol assuming any of the three previous values). Moreover, operators=$_\exists$, and =$_\forall$ can be used only when the class expression appears in <exp>. The meaning of =$_\exists$(=$_\forall$) is that some (all) attributes corresponding to expression <exp> are equal to <value>.

Example. Consider the operator MATCH(Rule_Set, Body $\supseteq$ {(1004=#, 13=$\downarrow$, 15=*, 16 $\neq\downarrow$, G7=$_\exists\uparrow$), Head=(*= $\uparrow$)} that returns all the rules satisfying the following conditions: The body of these rules have gene 1004 remaining unchanged, gene 13 being downregulated, gene 15 must be present in the rule body, gene 16 not being downregulated, and at least one member gene from the group of genes G7 being upregulated. Also, the head of the rule should refer to any upregulated gene.

2. MISMATCH (S, T). This operator selects all the logical rules in set S that do not match pattern template T described above, and returns this set of rules. The structure of template T is the same as in point 1 described above.

Example. Operator MISMATCH(Rule_Set, Body $\supseteq$ {(133=*, 236=*, *=$\downarrow$), Head=(1012=$\uparrow$)} returns all the rules satisfying the following conditions: The body of these rules must not contain gene 133 or gene 236 or no gene in the body of the rule should be downregulated. The head of the rule must not contain gene 1012 being unregulated.

3. CONTRADICT(S, T). This operator selects all the logical rules in set S that contradict the template T and returns this set of rules. For example, template T can be defined as in point 1 above, or using generalized impressions. The CONTRADICT operator takes the rules S and selects those that match the body of the template T, but do not match the head of the template.

Example. Consider the operator CONTRADICT(Rule_ Set, Body $\subseteq$ {(201=*, 456=$\uparrow$, 587=$\downarrow$, $G_\uparrow$=$_\exists\uparrow$), Head= (1012=$\uparrow$)}. It returns all the rules contradicting the rule template specified as its second parameter. More specifically, a rule contradicts the specified template if the body of the rule "matches" the body of the template while the value of the attribute in the head of the rule does not match the one specified in the head of the template. For example, the rule

201=$\uparrow$, 587=$\downarrow$, $G_\uparrow$=$_\exists\uparrow$→1012=# contradicts the specified template, and therefore is selected by the CONTRADICT operator.

Clustering Operator

The clustering operator combines groups of similar logical rules together into clusters of rules using certain prespecified clustering criteria. Thereafter, these groups of similar rules are presented for further examination and processing.

Under a preferred embodiment of the instant invention, one method of grouping similar rules is by combining groups of biologically related attributes into mutually exclusive and collectively exhaustive classes of attributes $C_1, \ldots, C_n$ (i.e., each attribute $A_i$ belongs to one and only one class $C_j$) and then grouping all the rules $A_1$ and $A_2$ and ... and $A_m \rightarrow A$ into the same group if all the attributes $A_i$ of these rules belong to the same classes (i.e., the rules in the same group will have the same class structure). Moreover, the groups of biologically related attributes can be either specified directly by a biologist or can be taken from the existing classification hierarchies.

For example, if these attributes are genes of biological organisms, then many of these organisms have already well-defined classifications of their genes that are based on their functions, categories, and other biologically relevant classifications. For example, if two genes A and B belong to the same "DNA Repair" category, then any rules referring to these two genes are indistinguishable in terms of that category.

Data Mapping Operators

In addition to the filtering operations, the instant invention further involves the introduction of data mapping operators TRANS_MATCH(D,T,C) and TRANS_MISMATCH(D,T, C). These operators allow the user to identify which records in the data match or mismatch the specified rule or a rule template, allowing for future experiment planning and closer analysis of this experimental data.

4. TRANS_MATCH(D,T,C). Given a data set D and a rule template T (as defined for filtering operator in point 1), the operator determines which records within the data set D match the rules corresponding to the rule template T. Condition C is of two types—"for all" and "for any". A record t matches the template T for condition C="for all" if this record matches all of the rules corresponding to template T. Similarly, a record t matches the template T for condition C="for any" if this record matches one or more of the rules corresponding to template T.

Example. TRANS_MATCH(Data_Set, Body={(187=$\downarrow$, 343=$\uparrow$), Head=(101=$\uparrow$), "for all")} returns all the records t from Data_Set for which the rule template is true (each of its rules holds on record t).

5. TRANS_MISMATCH(D,T,C). Given a data set D and a rule template T (as defined for filtering operator in point 1), the operator determines which records within the data set D do not match the rules specified by template T. Condition C is of two types—"for all" and "for any". A record t mismatches the template T for condition C="for all" if this record does not match all of the rules corresponding to template T. Similarly, a record t mismatches the template T for condition C="for any" if this record does not match one or more of the rules corresponding to template T.

Example. TRANS_MISMATCH(Data_Set, Body={ (187=$\downarrow$, 343=$\uparrow$), Head=(101=$\uparrow$), "for any"} returns all the records mismatching some of the rules corresponding to the template {Body=(187=↓, 343=↑), Head=(101=↑)}.

Data Characterization Operators

The data characterization operators work with a structure defined for a set of records in the data set D. This structure S partitions the set of records into a mutually exclusive and collectively exhaustive set of records. The structure S can take a variety of forms, including, but not limited to trees, directed acyclic graphs (DAGs), time series structures. The structure S can be organized in a hierarchy and hence can partition the set of records in a hierarchical fashion. Given this structure S, a set of rules R and the set of records D, the data characterization operator DATA_CHAR(D,S,R) works as follows.

6. DATA_CHAR(D,S,$R_{all}$). Each position P in structure S, determines the set of records $TR_P$ from the data set D corresponding to this position. The DATA_CHAR operator determines the set of rules from the rule set $R_{all}$, that hold (with a pre-specified levels of statistical strength, including confidence and/or support) on the set of records $TR_P$. Finally, the DATA_CHAR operator associates these rules with each position P in structure S.

Figure 3:
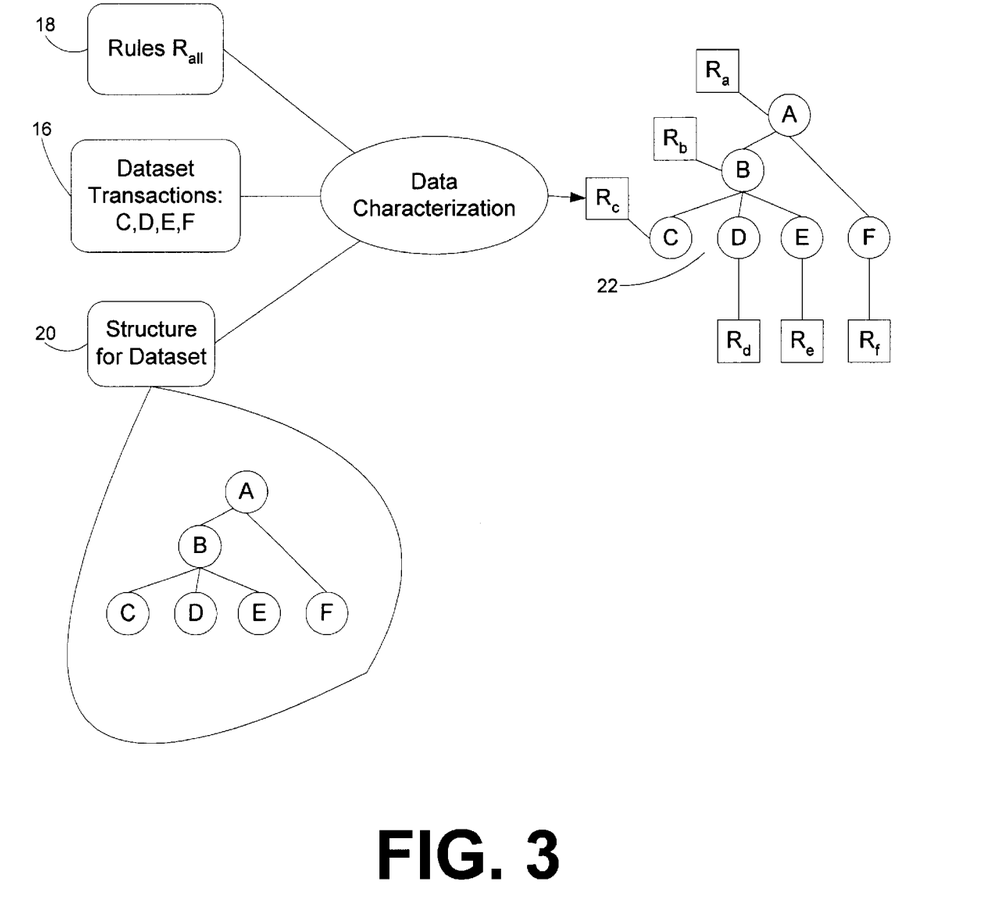
FIG. 3 is logical relational diagram showing the data characterization filter in accordance with a preferred embodiment of the invention.

Example. Consider the diagram presented in FIG. 3. In FIG. 3, the set of records D (specified by Box 16 and called Dataset) contains records C, D, E, and F. The structure S (Box 20) is defined by the tree with records C, D, E, and F as the leaves of the tree and nodes A and B as intermediate members of the structural hierarchy S. Moreover, the set of all rules $R_{all}$ is specified in Box 18 in FIG. 3. The data characterization operator assigns the rules from the set $R_{all}$ to each node of the structure S as follows. For each node of the structure S, take all the records T that are descendants of this node (e.g. for node B, this set T contains records C, D, and E). Then the DATA_CHAR operator selects all the rules in $R_{all}$ that hold on this set of records T and assigns it to the node. In Box 22 of FIG. 3, the assigned rules are represented with square boxes $R_a$–$R_f$.

It should be understood that the preferred embodiments and examples described are for illustrative purposes only and are not to be construed as limiting the scope of the present invention which is properly delineated only in the appended claims.

I claim:

1. A method for the analysis of biological, medical or biochemical data having values for each of a plurality of attributes, comprising:
    (a) receiving the data and entering such data into a storage arrangement in accordance with the values and attributes of the data;
    (b) determining at least one discrete bin in correlation with at least one of the attributes for the data in accordance with the values of the data entered in the storage arrangement for each of said at least one attributes;
    (c) associating the data having the at least one attribute in the storage arrangement with the correlating at least one discrete bins;
    (d) data mining the associated data in the storage arrangement to determine at least one set of applicable logical rules;
    (e) iteratively processing said applicable logical rules to determine a subset thereof, comprising a set of processed, applicable logical rules; and
    (f) outputting an output selected from the group consisting of the applicable logical rules, the processed, applicable logical rules, the associated data, the raw data, and combinations thereof.

2. The method of claim 1, wherein the data is numeric, and the steps (a) through (e) further comprise, prior to the step (c) of associating the data, discretizing the numeric data in the storage arrangement by tagging each of the data points in the storage arrangement with a tag indicative of the appropriate bin in which each such point is to be associated.

3. The method of claim 1, wherein the iterative processing and outputting steps (e) and (f) comprise the steps of:
    (a) retrieving the applicable logical rules produced by the data mining step (d);
    (b) selecting at least one operator from a group of operators to apply to the applicable logical rules;
    (c) processing the applicable logical rules in accordance with the at least one selected operator to create the processed, applicable logical rules;
    (d) presenting said output;
    (e) determining whether to further process the applicable logical rules; and
    (f) when the result of the determining step is to further process, then further processing of the applicable logical rules, comprising:
        1. determining a portion of the applicable logical rules to further process;
        2. retrieving the portion of the applicable logical rules in accordance with the determination step (f)(1);
        3. selecting at least one operator from the group of operators to apply to the portion of the applicable logical rules retrieved by way of step (f)(2);
        4. processing the portion of the applicable logical rules in accordance with the at least one selected operator to create the processed, applicable logical rules;
        5. presenting said output;
        6. determining whether to perform additional processing of the applicable logical rules; and
        7. repeating steps (f)(1) through (f)(7) when the result of said determination is to further process the applicable logical rules.

4. The method of claim 3, wherein the group of operators includes at least one filtering operator.

5. The method of claim 4, wherein the at least one filtering operator is selected from the group consisting of MATCH (S,T), MISMATCH(S,T), and CONTRADICT(S,T) wherein S is a set of logical rules, and T is a template.

6. The method of claim 3, wherein the group of operators includes at least one clustering operator.

7. The method of claim 3, wherein the group of operators includes at least one data mapping operator.

8. The method of claim 7, wherein the at least one data mapping operator is selected from the group consisting of TRANS_MATCH(D,T,C) and TRANS_MISMATCH(D,T,C) wherein D is a data set, T is a template, and C is a matching condition "for all" or "for any."

9. The method of claim 3, wherein the group of operators includes at least one data characterization operator.

10. The method of claim 9, wherein the at least one data characterization operator is DATA_CHAR(D,S,R), wherein D is a set of records, S is a structure, and R is a set of rules.

11. The method of claim 1, wherein the storage arrangement comprises a relational database.

12. The method of claim 1, wherein the number of bins is a number "n" and wherein $1 < n \leq 100$, preferably $n \leq 10$, and more preferably, $n=3$.

13. The method of claim 1, wherein the attributes have values selected from the group consisting of unchanged, upregulated, downregulated, and combinations thereof.

14. A system for providing logical rules in connection with biological, medical or biochemical data having values for each of a plurality of attributes, comprising:

(a) receiving means for receiving the data and entering such data into a storage arrangement in accordance with the values and attributes of the data;

(b) calculating means for determining discrete bins for at least one of the attributes of the data in accordance with the values of the data entered in the storage arrangement for each of said at least one attributes;

(c) re-organizing means for re-organizing the data in the storage arrangement in accordance with the discrete bins;

(d) data mining means for mining the organized data in the storage arrangement to determine applicable logical rules;

(e) iterative processing and presentation means for iteratively processing said applicable logical rules to determine a subset thereof, comprising a set of processed, applicable logical rules; and (f) outputting means for outputting an output selected from the group consisting of the applicable logical rules, the processed, applicable logical rules, the associated data, the raw data, and combinations thereof.

15. The system of claim 14, wherein the data is numeric, further comprising, prior to the re-organizing means, discretizing means for discretizing the numeric data in the storage arrangement by tagging each of the data points in the storage arrangement with a tag indicative of the appropriate bin in which each such point is found.

16. The system of claim 14, wherein the iterative processing and outputting means provides further processing in accordance with the following steps:

(a) retrieving the applicable logical rules produced by the data mining step (d);

(b) selecting at least one operator from a group of operators to apply to the applicable logical rules;

(c) processing the applicable logical rules in accordance with the at least one selected operator to create the processed, applicable logical rules;

(d) presenting said output;

(e) determining whether to further process the applicable logical rules; and (f) when the result of the determining step is to further process, then further processing of the applicable logical rules, comprising:

1. determining a portion of the applicable logical rules to further process;
2. retrieving the portion of the applicable logical rules in accordance with the determination step (f)(1);
3. selecting at least one operator from the group of operators to apply to the portion of the applicable logical rules retrieved by way of step (f)(2);
4. processing the portion of the applicable logical rules in accordance with the at least one selected operator to create the processed, applicable logical rules;
5. presenting said output;
6. determining whether to perform additional processing of the applicable logical rules; and
7. repeating steps (f)(1) through (f)(7) when the result of said determination is to further process the applicable logical rules.

17. The system of claim 16, wherein said group of operators is selected from the group consisting of filtering operators, clustering operators, data mapping operators, data characterization operators, and combinations thereof.

18. The system of claim 17, wherein the at least one operator is a filtering operator selected from the group consisting of MATCH(S,T), MISMATCH(S,T), and CONTRADICT(S,T), wherein S is a set of logical rules and T is a template.

19. The system of claim 17, wherein the at least one operator is a data mapping operator selected from the group consisting of TRANS_MATCH(D,T,C) and TRANS_MISMATCH(D,T,C) wherein D is a data set, T is a template, and C is a matching condition "for all" or "for any."

20. The system of claim 17, wherein the at least one operator is a data characterization operator and is DATA_CHAR(D,S,R), wherein D is a set of records, S is a structure, and R is a set of rules.

21. The system of claim 14, wherein the storage arrangement comprises a relational database.

22. The system of claim 14, wherein the number of bins is a number "n" and wherein $1 < n \leq 100$, preferably $n \leq 10$, and more preferably n=3.

23. The system of claim 14, wherein the attributes are selected from the group consisting of unchanged, upregulated and downregulated.

* * * * *